United States Patent
Murakami et al.

(10) Patent No.: US 12,171,620 B2
(45) Date of Patent: Dec. 24, 2024

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventors: Hiroshi Murakami, Kanagawa (JP); Katsuya Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 157 days.

(21) Appl. No.: 18/161,815

(22) Filed: Jan. 30, 2023

(65) Prior Publication Data

US 2023/0285007 A1    Sep. 14, 2023

(30) Foreign Application Priority Data

Mar. 14, 2022 (JP) ................. 2022-038847

(51) Int. Cl.
*A61B 8/00* (2006.01)
(52) U.S. Cl.
CPC .................. *A61B 8/56* (2013.01); *A61B 8/54* (2013.01); *A61B 8/4444* (2013.01)
(58) Field of Classification Search
CPC ............ A61B 8/56; A61B 8/54; A61B 8/4444
See application file for complete search history.

(56) References Cited

U.S. PATENT DOCUMENTS

| | | | | |
|---|---|---|---|---|
| 8,417,979 | B2 * | 4/2013 | Maroney | G06F 1/3268 713/323 |
| 8,568,325 | B2 * | 10/2013 | Moritz | A61B 8/56 600/407 |
| 10,588,607 | B2 * | 3/2020 | Dickie | A61B 8/4472 |
| 2019/0175149 | A1 | 6/2019 | Dickie et al. | |

FOREIGN PATENT DOCUMENTS

| | | |
|---|---|---|
| EP | 2915490 A1 | 9/2015 |
| JP | 2011-072703 A | 4/2011 |

OTHER PUBLICATIONS

The extended European search report issued by the European Patent Office on Jul. 27, 2023, which corresponds to European Patent Application No. 23158275.0-1126 and is related to U.S. Appl. No. 18/161,815.

* cited by examiner

*Primary Examiner* — Joseph M Santos Rodriguez
(74) *Attorney, Agent, or Firm* — Studebaker & Brackett PC

(57) ABSTRACT

There are provided an ultrasound diagnostic apparatus and a control method for an ultrasound diagnostic apparatus capable of activating an ultrasound probe only by an operation of an apparatus main body and achieving power saving. The ultrasound probe includes an ultrasound unit that acquires ultrasound image data, a probe-side first communication circuit and a probe-side second communication circuit each of which performs wireless communication with the apparatus main body and which have transmission capacities different from each other and power consumptions different from each other, and a power supply controller that selects one communication circuit among the probe-side first communication circuit and the probe-side second communication circuit according to a power supply mode of the ultrasound probe and performs wireless communication with the apparatus main body by using the selected communication circuit.

20 Claims, 6 Drawing Sheets

FIG. 5
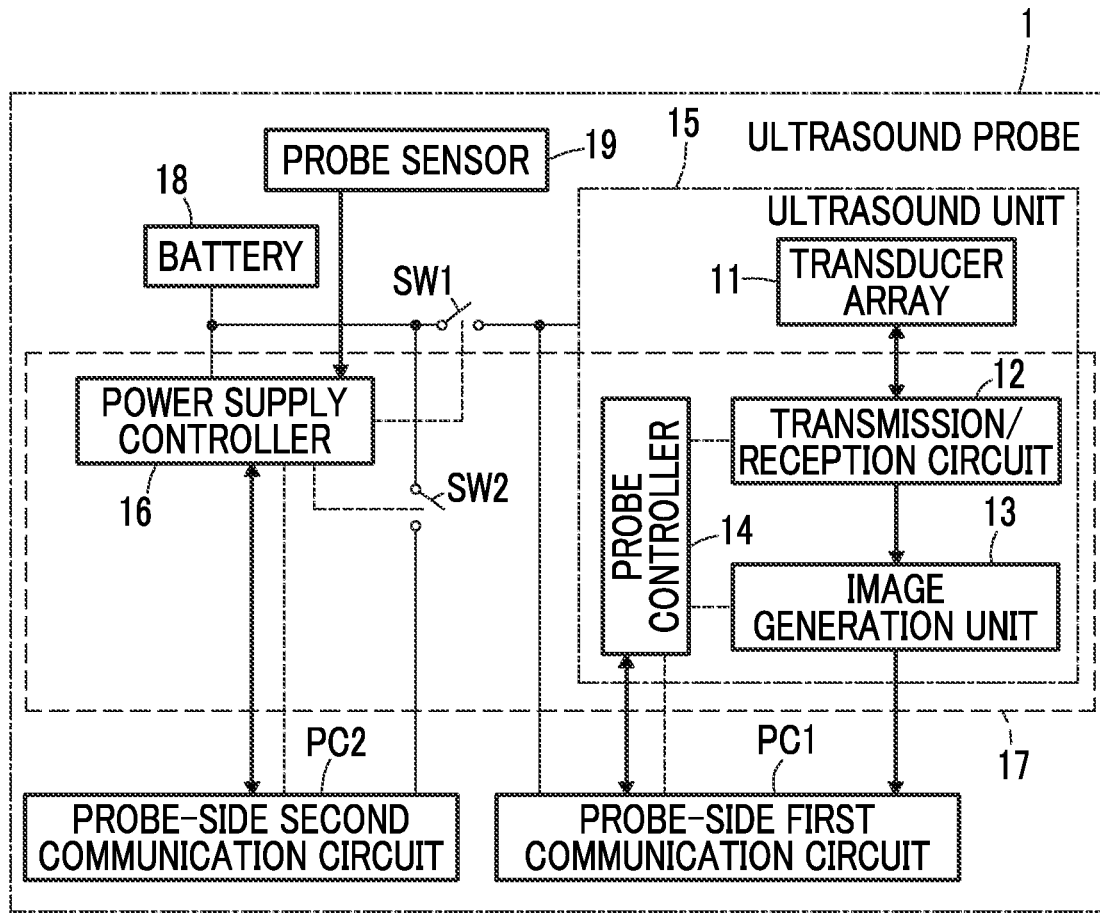
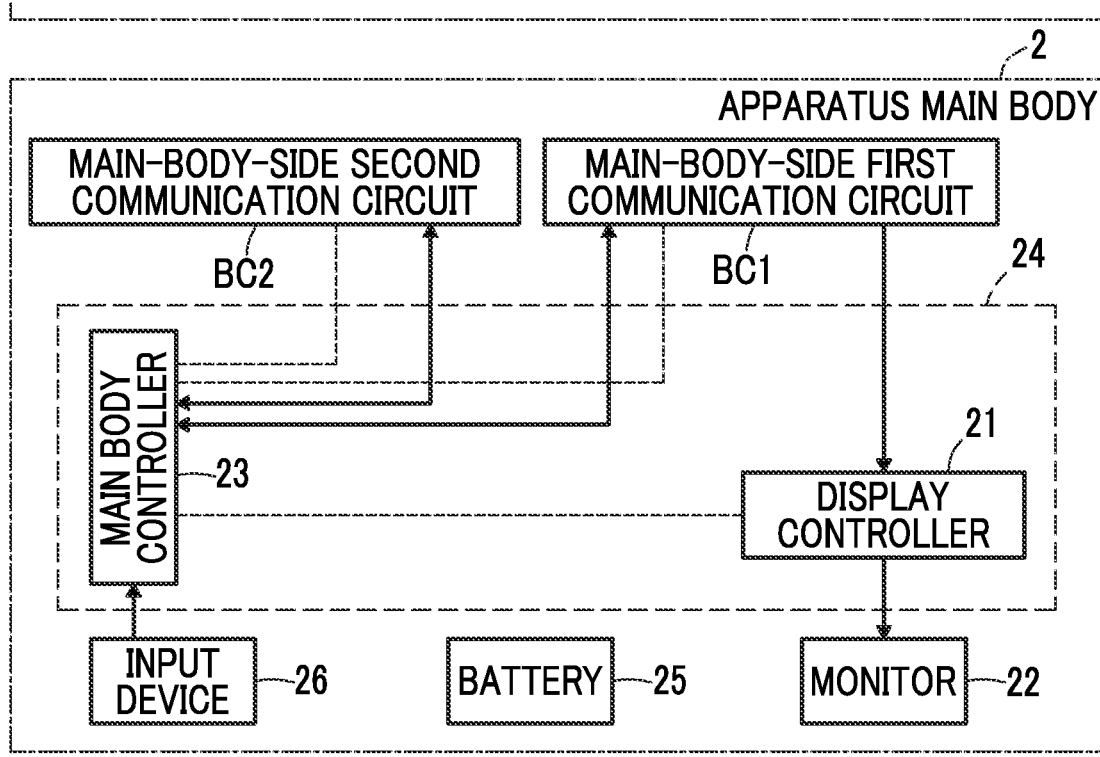

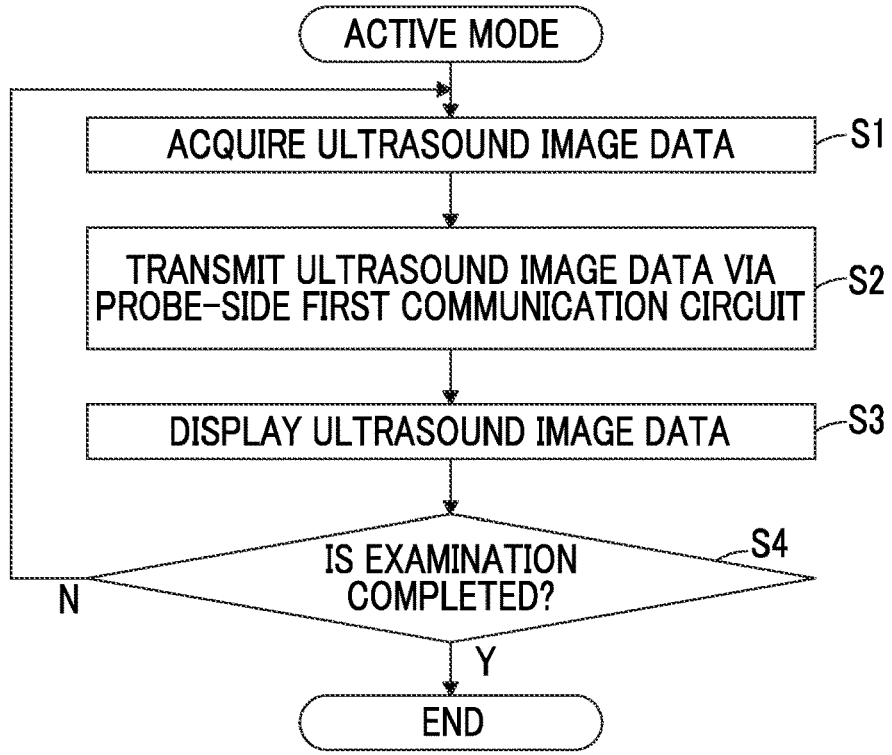
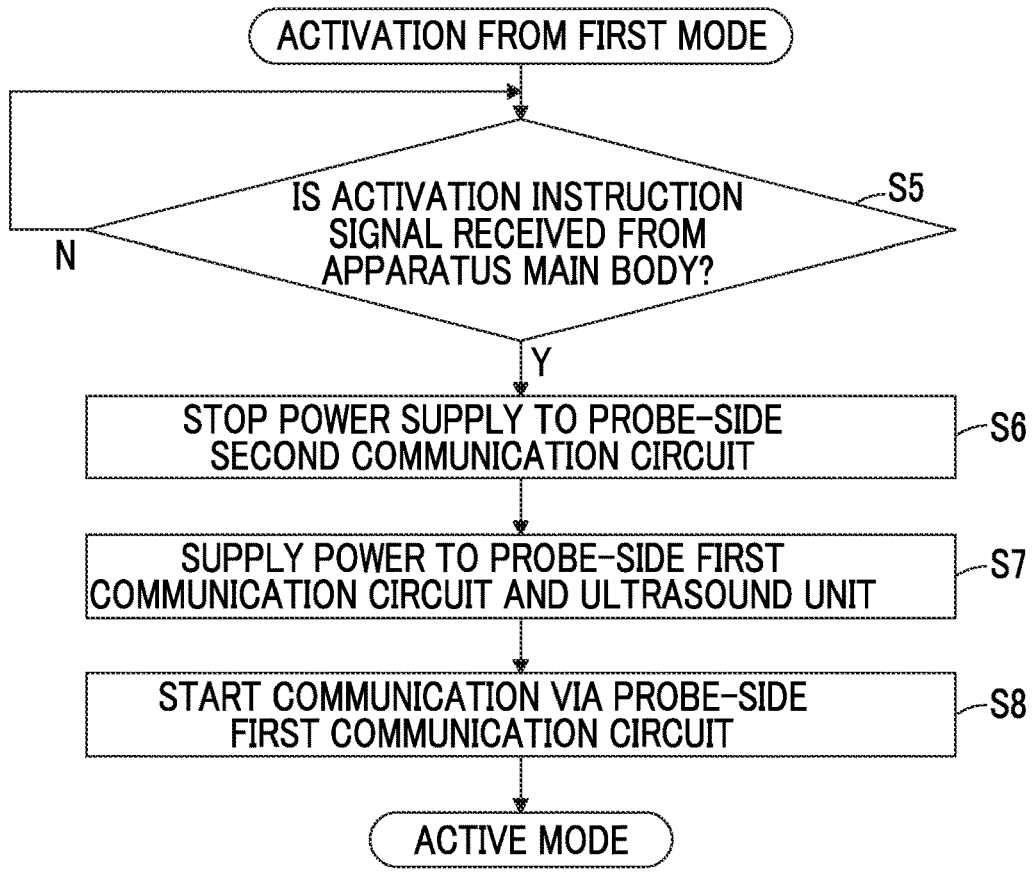

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

The present application claims priority under 35 U.S.C. § 119 to Japanese Patent Application No. 2022-038847, filed on Mar. 14, 2022. The above application is hereby expressly incorporated by reference, in its entirety, into the present application.

BACKGROUND OF THE INVENTION

1. Field of the Invention

The present invention relates to an ultrasound diagnostic apparatus and a control method for an ultrasound diagnostic apparatus, and in particular, relates to power saving of an ultrasound diagnostic apparatus in which an ultrasound probe and an apparatus main body are connected to each other by wireless communication.

2. Description of the Related Art

In related art, an ultrasound diagnostic apparatus using ultrasound images has been put into practical use in a medical field. In general, such an ultrasound diagnostic apparatus includes an ultrasound probe in which a transducer array is provided and an apparatus main body connected to the ultrasound probe. An ultrasound beam is transmitted from the transducer array of the ultrasound probe toward a subject, an ultrasound echo from the subject is received by the transducer array, and a reception signal is electrically processed. Thereby, an ultrasound image is generated, and the ultrasound image is displayed on a monitor of the apparatus main body.

In recent years, an ultrasound diagnostic apparatus, in which operability and maneuverability of an ultrasound probe are improved by connecting an ultrasound probe and an apparatus main body by wireless communication, has been developed.

In such an ultrasound diagnostic apparatus, generally, a built-in battery is provided in the ultrasound probe, and the ultrasound probe is activated by power from the battery. For this reason, power saving of the ultrasound probe is required such that the ultrasound probe can be activated for a long period of time.

For example, JP2011-072703A discloses an ultrasound diagnostic apparatus in which an ultrasound probe includes an acceleration sensor, in which the acceleration sensor detects that the ultrasound probe is moved, and in which power is supplied to each unit of the ultrasound probe such as a transmission beam former. According to the ultrasound diagnostic apparatus, in a case where the acceleration sensor detects that the ultrasound probe is gripped by an inspector, each unit of the ultrasound probe can be operated, and thus it is possible to achieve power saving.

SUMMARY OF THE INVENTION

However, in order to shorten an activation time of the ultrasound probe, it is desired to activate the ultrasound probe only by an operation of the apparatus main body without requiring operations of both the ultrasound probe and the apparatus main body. In this case, the ultrasound probe is in a standby mode until an activation signal is received from the apparatus main body, and the standby mode is switched to an active mode in a case where an activation signal is received.

In wireless communication between the ultrasound probe and the apparatus main body, ultrasound image data having a large data amount is transmitted. For this reason, for example, a communication method such as Wi-Fi (registered trademark) is adopted. However, in a case where Wi-Fi connection with a high power consumption is maintained in the standby mode, the battery is greatly consumed, and a standby time in the standby mode is shortened. As a result, this causes interference in ultrasound diagnosis.

The present invention has been made to solve such a problem in the related art, and an object of the present invention is to provide an ultrasound diagnostic apparatus and a control method for an ultrasound diagnostic apparatus capable of activating an ultrasound probe only by an operation of an apparatus main body and achieving power saving.

In order to achieve the above object, according to an aspect of the present invention, there is provided an ultrasound diagnostic apparatus including: an ultrasound probe; and an apparatus main body that is wirelessly connected to the ultrasound probe, in which the ultrasound probe includes an ultrasound unit that acquires ultrasound image data by transmitting and receiving ultrasound waves, a plurality of probe-side communication circuits each of which performs wireless communication with the apparatus main body and which have transmission capacities different from each other and power consumptions different from each other, and a power supply controller that selects one probe-side communication circuit among the plurality of probe-side communication circuits according to a power supply mode of the ultrasound probe and performs wireless communication with the apparatus main body by using the selected probe-side communication circuit, the power supply mode of the ultrasound probe includes an active mode in which an operation of the ultrasound unit is enabled and a standby mode in which an operation of the ultrasound unit is disabled and a power consumption is lower than a power consumption in the active mode, and the power supply controller switches the power supply mode from the standby mode to the active mode in a case where the ultrasound probe receives an activation control signal from the apparatus main body.

Preferably, the plurality of probe-side communication circuits include a probe-side first communication circuit that is selected by the power supply controller and transmits the ultrasound image data acquired by the ultrasound unit to the apparatus main body in a case where the power supply mode is the active mode, and a probe-side second communication circuit that is selected by the power supply controller and operates with a power consumption lower than a power consumption of the probe-side first communication circuit in a case where the power supply mode is the standby mode.

Further, preferably, the ultrasound probe includes a built-in battery, the power supply controller supplies power from the battery to the ultrasound unit and the probe-side first communication circuit and stops power supply to the probe-side second communication circuit in a case where the power supply mode is the active mode, and the power supply controller supplies power from the battery to the probe-side second communication circuit and stops power supply to the ultrasound unit and the probe-side first communication circuit in a case where the power supply mode is the standby mode.

The standby mode further includes a first mode and a second mode in which a power consumption is lower than a power consumption in the first mode. The power supply controller is configured to supply power from the battery to the probe-side second communication circuit in a case where the power supply mode is the first mode. The power supply controller is configured to stop power supply from the battery to the probe-side second communication circuit in a case where the power supply mode is the second mode.

Alternatively, the standby mode further includes a first mode and a second mode in which a power consumption is lower than a power consumption in the first mode. The power supply controller supplies power from the battery to the probe-side second communication circuit in a case where the power supply mode is the first mode and in a case where the power supply mode is the second mode. The power supply controller controls the probe-side second communication circuit in a case where the power supply mode is the second mode such that the ultrasound probe performs wireless communication with the apparatus main body at a communication interval longer than a communication interval in a case where the power supply mode is the first mode.

The ultrasound probe may include a probe sensor for detecting that the ultrasound probe is gripped or moved by a user. In a case where the power supply mode is the second mode and the probe sensor detects that the ultrasound probe is gripped or moved, the power supply controller may be configured to switch the power supply mode from the second mode to the first mode, and the ultrasound probe may be configured to transmit a pairing request signal to the apparatus main body via the probe-side second communication circuit. The power supply controller may be configured to switch the power supply mode from the standby mode to the active mode in a case where the ultrasound probe receives a pairing completion notification signal as the activation control signal from the apparatus main body via the probe-side second communication circuit.

Preferably, the probe sensor consists of an acceleration sensor or a contact sensor provided on the ultrasound probe.

The power supply controller may be configured to switch the power supply mode from the standby mode to the active mode in a case where the power supply mode is the first mode and the ultrasound probe receives an activation instruction signal as the activation control signal from the apparatus main body via the probe-side second communication circuit.

Preferably, a time required to transition the power supply mode from the first mode to the active mode is shorter than a time required to transition the power supply mode from the second mode to the active mode.

Preferably, the apparatus main body includes a plurality of main-body-side communication circuits corresponding to the plurality of probe-side communication circuits. Preferably, the plurality of main-body-side communication circuits include a main-body-side first communication circuit that performs wireless communication with the probe-side first communication circuit, and a main-body-side second communication circuit that performs wireless communication with the probe-side second communication circuit.

In this case, the activation control signal is transmitted from the apparatus main body to the ultrasound probe via the main-body-side second communication circuit and the probe-side second communication circuit.

According to another aspect of the present invention, there is provided a control method for an ultrasound diagnostic apparatus including an ultrasound probe, which includes a plurality of probe-side communication circuits having transmission capacities different from each other and power consumptions different from each other, and an apparatus main body which is wirelessly connected to the ultrasound probe, the method including: selecting one probe-side communication circuit among the plurality of probe-side communication circuits according to a power supply mode of the ultrasound probe; and performing wireless communication between the ultrasound probe and the apparatus main body by using the selected probe-side communication circuit, in which the power supply mode of the ultrasound probe includes an active mode in which an operation of an ultrasound unit is enabled and a standby mode in which an operation of the ultrasound unit is disabled and a power consumption is lower than a power consumption in the active mode, the ultrasound unit acquiring ultrasound image data by transmitting and receiving ultrasound waves, and the power supply mode is switched from the standby mode to the active mode in a case where the ultrasound probe receives an activation control signal from the apparatus main body.

According to the present invention, an ultrasound diagnostic apparatus includes an ultrasound probe and an apparatus main body that is wirelessly connected to the ultrasound probe. The ultrasound probe includes a plurality of probe-side communication circuits each of which performs wireless communication with the apparatus main body and which have transmission capacities different from each other and power consumptions different from each other and a power supply controller that selects one probe-side communication circuit among the plurality of probe-side communication circuits according to a power supply mode of the ultrasound probe and performs wireless communication with the apparatus main body by using the selected probe-side communication circuit. The power supply controller switches a power supply mode from a standby mode to an active mode in a case where the ultrasound probe receives an activation control signal from the apparatus main body. Therefore, it is possible to activate the ultrasound probe only by an operation of the apparatus main body and achieve power saving.

BRIEF DESCRIPTION OF THE DRAWINGS

FIG. 5 is a block diagram illustrating a configuration of the ultrasound diagnostic apparatus according to the embodiment 1 in a second mode.

FIG. 6 is a flowchart illustrating an operation of the ultrasound diagnostic apparatus according to the embodiment 1 in the active mode.

FIG. 7 is a flowchart illustrating an operation of the ultrasound diagnostic apparatus according to the embodiment 1 in a case of being activated from the first mode.

DESCRIPTION OF THE PREFERRED EMBODIMENTS

Hereinafter, embodiments of the present invention will be described with reference to the accompanying drawings.

A description of components to be described below is based on a representative embodiment of the present invention. On the other hand, the present invention is not limited to such an embodiment.

Note that, in this specification, a numerical range represented by using "to" means a range including numerical values described before and after "to", both ends inclusive, as a lower limit value and an upper limit value.

In this specification, it is assumed that terms "identical" and "same" include an error margin which is generally allowed in the technical field.

Embodiment 1

Figure 1:
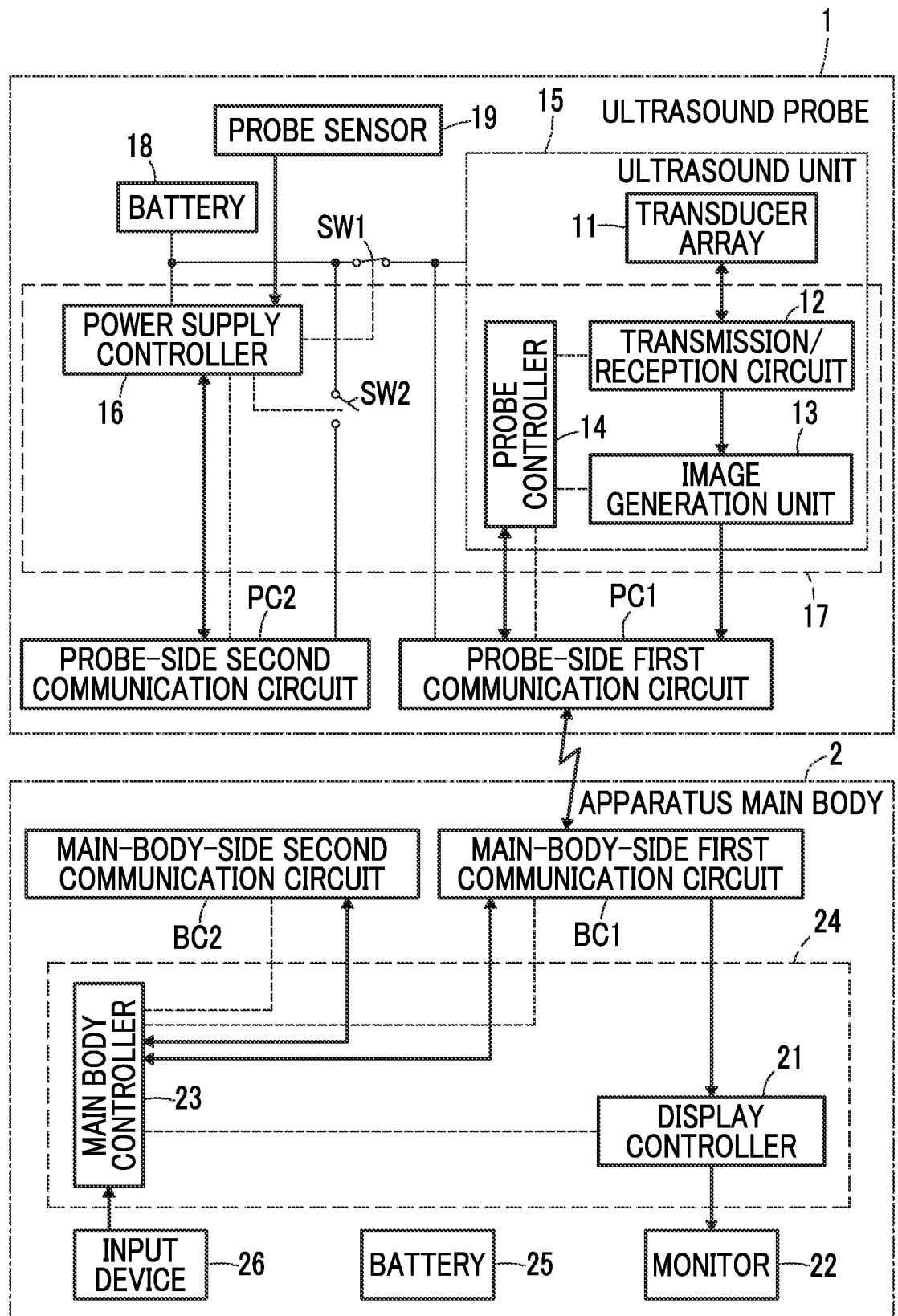
FIG. 1 is a block diagram illustrating a configuration of an ultrasound diagnostic apparatus according to an embodiment 1 of the present invention in an active mode.

FIG. 1 illustrates a configuration of an ultrasound diagnostic apparatus according to an embodiment 1 of the present invention. The ultrasound diagnostic apparatus is an ultrasound diagnostic apparatus which includes an ultrasound probe 1 and an apparatus main body 2 connected to the ultrasound probe 1 and in which the ultrasound probe 1 and the apparatus main body 2 are wirelessly connected to each other.

The ultrasound probe 1 includes a transducer array 11, and a transmission/reception circuit 12 and an image generation unit 13 are sequentially connected to the transducer array 11. A probe controller 14 is connected to the transmission/reception circuit 12 and the image generation unit 13, and an ultrasound unit 15 is configured with the transducer array 11, the transmission/reception circuit 12, the image generation unit 13, and the probe controller 14.

In addition, the ultrasound probe 1 includes a power supply controller 16. A probe-side first communication circuit PC1 is connected to the probe controller 14, and a probe-side second communication circuit PC2 is connected to the power supply controller 16.

A probe-side processor 17 is configured with the transmission/reception circuit 12, the image generation unit 13, the probe controller 14, and the power supply controller 16.

Further, the ultrasound probe 1 includes a battery 18, and the power supply controller 16 is connected to the battery 18. In addition, the ultrasound unit 15 and the probe-side first communication circuit PC1 are connected to the battery 18 via a first switch SW1. Similarly, the probe-side second communication circuit PC2 is connected to the battery 18 via a second switch SW2.

Further, a probe sensor 19 is provided on the ultrasound probe 1, and the probe sensor 19 is connected to the power supply controller 16.

On the other hand, the apparatus main body 2 includes a main-body-side first communication circuit BC1 and a main-body-side second communication circuit BC2 corresponding to the probe-side first communication circuit PC1 and the probe-side second communication circuit PC2 of the ultrasound probe 1. A display controller 21 and a monitor 22 are sequentially connected to the main-body-side first communication circuit BC1. In addition, a main body controller 23 is connected to the display controller 21, the main-body-side first communication circuit BC1, and the main-body-side second communication circuit BC2.

A main-body-side processor 24 is configured with the display controller 21 and the main body controller 23.

Further, the apparatus main body 2 includes a battery 25 and an input device 26, and the input device 26 is connected to the main body controller 23.

The transducer array 11 of the ultrasound probe 1 includes a plurality of ultrasound transducers which are one-dimensionally or two-dimensionally arranged. Each of these transducers transmits an ultrasound wave according to a drive signal supplied from the transmission/reception circuit 12, receives a reflected wave from a subject, and outputs an analog reception signal. Each transducer is configured by, for example, forming electrodes on both ends of a piezoelectric body such as a piezoelectric ceramic represented by lead zirconate titanate (PZT), a polymeric piezoelectric element represented by poly vinylidene di fluoride (PVDF), or a piezoelectric single crystal represented by a lead magnesium niobate-lead titanate (PMN-PT) solid solution.

Figure 2:
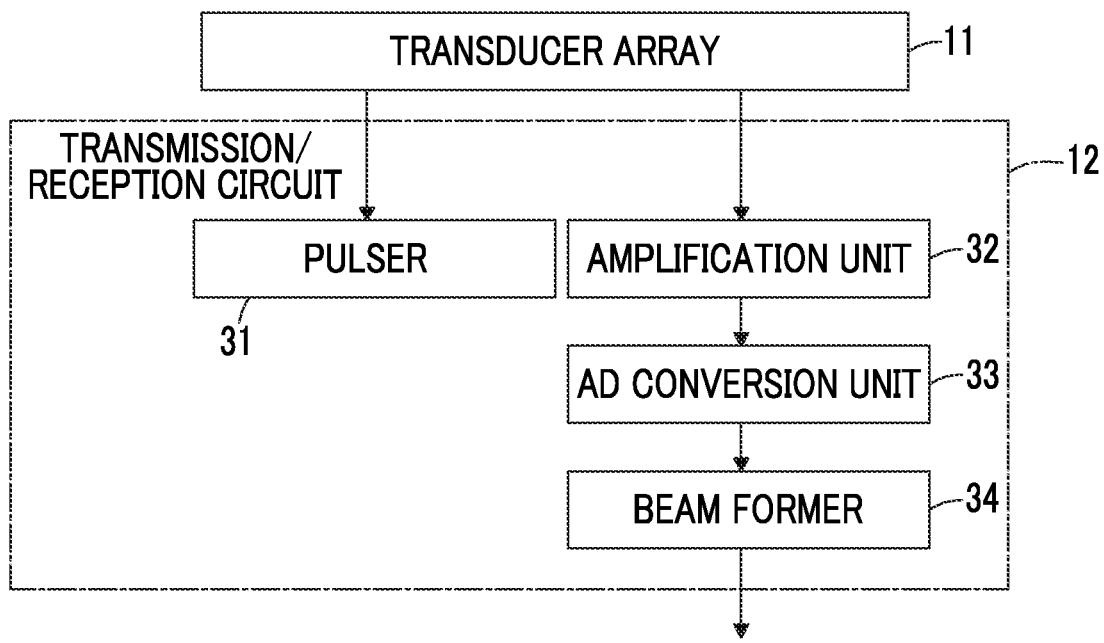
FIG. 2 is a block diagram illustrating an internal configuration of a transmission/reception circuit according to the embodiment 1.

The transmission/reception circuit 12 transmits an ultrasound wave from the transducer array 11 and generates a sound wave signal based on the reception signal acquired by the transducer array 11 under a control of the probe controller 14. As illustrated in FIG. 2, the transmission/reception circuit 12 includes a pulser 31 connected to the transducer array 11, an amplification unit 32 sequentially connected in series to the transducer array 11, an analog-to-digital (AD) conversion unit 33, and a beam former 34.

The pulser 31 includes, for example, a plurality of pulse generators, adjusts a delay amount of each drive signal based on a transmission delay pattern which is selected according to a control signal from the probe controller 14 such that ultrasound waves to be transmitted from the plurality of transducers of the transducer array 11 form ultrasound beams, and supplies each drive signal with the adjusted delay amount to the plurality of transducers. In this way, in a case where a voltage having a pulse shape or a continuous wave shape is applied to the electrodes of the transducers of the transducer array 11, the piezoelectric body expands and contracts. Thereby, ultrasound waves having a pulse shape or a continuous wave shape are generated from each transducer, and thus an ultrasound beam is formed from a composite wave of these ultrasound waves.

The transmitted ultrasound beam is reflected by an object such as a portion of a subject, and an ultrasound echo propagates toward the transducer array 11 of the ultrasound probe 1. The ultrasound echo which propagates toward the transducer array 11 in this way is received by each transducer included in the transducer array 11. At this time, in a case where the propagating ultrasound echo is received, each transducer included in the transducer array 11 expands and contracts. Thereby, a reception signal as an electrical signal is generated, and these reception signals are output to the amplification unit 32.

The amplification unit 32 amplifies the signal which is input from each transducer included in the transducer array 11, and transmits the amplified signal to the AD conversion unit 33. The AD conversion unit 33 converts the signal transmitted from the amplification unit 32 into pieces of digital reception data, and transmits the pieces of reception data to the beam former 34. The beam former 34 performs so-called reception focus processing by applying and adding a delay to each of the pieces of reception data which is converted by the AD conversion unit 33 according to a sound velocity or a sound velocity distribution which is set based on a reception delay pattern selected according to a control signal from the probe controller 14. By this reception focus processing, a sound wave signal obtained by performing phasing addition on each of the pieces of reception data which is converted by the AD conversion unit 33 and narrowing down a focus of the ultrasound echo is acquired.

Figure 3:
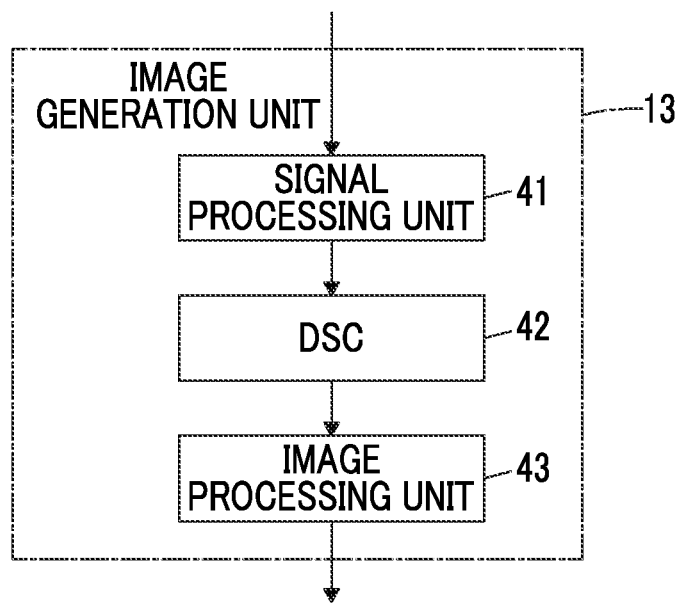
FIG. 3 is a block diagram illustrating an internal configuration of an image generation unit according to the embodiment 1.

As illustrated in FIG. 3, the image generation unit 13 has a configuration in which a signal processing unit 41, a digital scan converter (DSC) 42, and an image processing unit 43 are sequentially connected in series.

The signal processing unit 41 performs, on the sound wave signal transmitted from the transmission/reception circuit 12, correction of attenuation due to a distance according to a depth of a reflection position of the ultrasound wave and then performs envelope detection processing. Thereby, an ultrasound image signal (B-mode image signal), which is tomographic image information related to tissues in the subject, is generated.

The DSC 42 converts (raster-converts) the ultrasound image signal generated by the signal processing unit 41 into an image signal conforming to a normal television signal scanning method.

The image processing unit 43 performs various required image processing such as gradation processing on the ultrasound image signal which is input from the DSC 42, and then outputs data representing an ultrasound image (hereinafter, referred to as ultrasound image data) to the probe-side first communication circuit PC1.

In addition, the probe controller 14 controls the transmission/reception circuit 12 and the image generation unit 13 of the ultrasound unit 15 based on a program or the like stored in advance.

In this way, the ultrasound unit 15 configured with the transducer array 11, the transmission/reception circuit 12, the image generation unit 13, and the probe controller 14 acquires ultrasound image data representing an ultrasound image by transmitting and receiving ultrasound waves.

The probe-side first communication circuit PC1 and the probe-side second communication circuit PC2 respectively perform wireless communication with the apparatus main body 2 in a case where the ultrasound probe 1 and the apparatus main body 2 are wirelessly connected to each other, and have transmission capacities different from each other and power consumptions different from each other. Specifically, the probe-side first communication circuit PC1 performs wireless communication using, for example, a Wi-Fi (a registered trademark) communication method with a large transmission capacity and a high power consumption, while the probe-side second communication circuit PC2 performs wireless communication using, for example, a Bluetooth Low Energy (BLE, a registered trademark) communication method with a smaller transmission capacity and a lower power consumption as compared with the probe-side first communication circuit PC1.

The probe-side first communication circuit PC1 includes an antenna for transmitting and receiving radio waves, and wirelessly transmits the ultrasound image data to the main-body-side first communication circuit BC1 of the apparatus main body 2 by generating a transmission signal by modulating carriers based on the ultrasound image data generated by the image generation unit 13 and transmitting radio waves from the antenna by supplying the transmission signal to the antenna. As the carrier modulation method, amplitude shift keying (ASK), phase shift keying (PSK), quadrature phase shift keying (QPSK), 16 quadrature amplitude modulation (16 QAM), or the like is used.

Further, the probe-side first communication circuit PC1 transmits various signals transmitted from the probe controller 14 to the main-body-side first communication circuit BC1 of the apparatus main body 2, receives various signals transmitted from the main-body-side first communication circuit BC1 of the apparatus main body 2, and transmits the reception signals to the probe controller 14.

Similar to the probe-side first communication circuit PC1, the probe-side second communication circuit PC2 includes antenna for transmitting and receiving radio waves, transmits various signals transmitted from the power supply controller 16 to the main-body-side second communication circuit BC2 of the apparatus main body 2, receives various signals transmitted from the main-body-side second communication circuit BC2 of the apparatus main body 2, and transmits the various signals to the power supply controller 16.

The probe-side first communication circuit PC1 and the probe-side second communication circuit PC2 may be configured by sharing or reconfiguring a part or the whole of the circuits corresponding to each other.

The power supply controller 16 controls power supply from the battery 18 to the ultrasound unit 15, the probe-side first communication circuit PC1, and the probe-side second communication circuit PC2 by controlling opening and closing of the first switch SW1 and the second switch SW2 according to a power supply mode of the ultrasound probe 1.

For example, by closing the first switch SW1 and opening the second switch SW2, power is supplied from the battery 18 to the ultrasound unit 15 and the probe-side first communication circuit PC1, and thus the ultrasound unit 15 and the probe-side first communication circuit PC1 enter into an operable state. In addition, by stopping power supply from the battery 18 to the probe-side second communication circuit PC2, the probe-side second communication circuit PC2 enters into an operation-prohibited state.

In addition, by opening the first switch SW1 and closing the second switch SW2, power supply from the battery 18 to the ultrasound unit 15 and the probe-side first communication circuit PC1 is stopped, and thus the ultrasound unit 15 and the probe-side first communication circuit PC1 enter into an operation-prohibited state. In addition, by supplying power from the battery 18 to the probe-side second communication circuit PC2, the probe-side second communication circuit PC2 enters into an operable state.

That is, one of the probe-side first communication circuit PC1 and the probe-side second communication circuit PC2 is selected by the power supply controller 16, and is used for wireless communication with the apparatus main body 2.

Further, in a state where the first switch SW1 is open and the second switch SW2 is closed, in a case where an activation instruction signal transmitted from the main-body-side second communication circuit BC2 of the apparatus main body 2 is input as an activation control signal via the probe-side second communication circuit PC2, the power supply controller 16 opens the second switch SW2 and closes the first switch SW1, and thus the ultrasound unit 15 and the probe-side first communication circuit PC1 enter into an operable state.

In addition, in a state where both the first switch SW1 and the second switch SW2 are open, in a case where a detection signal indicating a detection result that the ultrasound probe 1 is gripped or moved is input from the probe sensor 19, the power supply controller 16 closes the second switch SW2, and transmits a pairing request signal to the main-body-side second communication circuit BC2 of the apparatus main body 2 via the probe-side second communication circuit PC2. Further, thereafter, in a case where a pairing completion notification signal transmitted from the main-body-side second communication circuit BC2 of the apparatus main body 2 is input as an activation control signal, the power supply controller 16 opens the second switch SW2 and closes the first switch SW1, and thus the ultrasound unit 15 and the probe-side first communication circuit PC1 enter into an operable state.

The battery 18 is configured with, for example, a lithium ion battery, and supplies power to the ultrasound unit 15, the power supply controller 16, the probe-side first communication circuit PC1, and the probe-side second communication circuit PC2 in the ultrasound probe 1.

The probe sensor 19 detects that the ultrasound probe 1 is gripped or moved by a user, and transmits a detection signal to the power supply controller 16. As the probe sensor 19, for example, an acceleration sensor or a contact sensor provided on the ultrasound probe 1 can be used. As the acceleration sensor, a sensor that detects acceleration of the ultrasound probe 1 by various methods such as a so-called optical method and an ultrasound method is used. As the contact sensor, a sensor that detects contact of a hand of a user with the ultrasound probe 1 by various methods such as a so-called capacitance method and a piezo-resistive method is used. In addition, a gyro sensor can also be used.

The probe-side processor 17 including the transmission/reception circuit 12, the image generation unit 13, the probe controller 14, and the power supply controller 16 of the ultrasound probe 1 is configured with a central processing unit (CPU) that executes various programs and a control program for causing the CPU to perform various processing. On the other hand, the probe-side processor 17 may be configured by using a field programmable gate array (FPGA), a digital signal processor (DSP), an application specific integrated circuit (ASIC), a graphics processing unit (GPU), or other integrated circuits (IC), or may be configured by using a combination thereof.

In addition, the transmission/reception circuit 12, the image generation unit 13, the probe controller 14, and the power supply controller 16 of the probe-side processor 17 can be partially or wholly integrated into one CPU or the like.

The main-body-side first communication circuit BC1 and the main-body-side second communication circuit BC2 of the apparatus main body 2 correspond to the probe-side first communication circuit PC1 and the probe-side second communication circuit PC2 of the ultrasound probe 1, perform wireless communication with the ultrasound probe 1 in a case where the apparatus main body 2 is wirelessly connected to the ultrasound probe 1, and have transmission capacities different from each other and power consumptions different from each other. Specifically, the main-body-side first communication circuit BC1 performs wireless communication with the probe-side first communication circuit PC1 of the ultrasound probe 1 using, for example, a Wi-Fi communication method with a large transmission capacity and a high power consumption. On the other hand, the main-body-side second communication circuit BC2 performs wireless communication with the probe-side second communication circuit PC2 of the ultrasound probe 1 using, for example, a BLE communication method with a relatively small transmission capacity and a relatively low power consumption.

The main-body-side first communication circuit BC1 includes an antenna for transmitting and receiving radio waves, receives, via the antenna, the transmission signal transmitted from the probe-side first communication circuit PC1 based on the ultrasound image data generated by the image generation unit 13 of the ultrasound probe 1, generates an ultrasound image by demodulating the received transmission signal, and transmits the ultrasound image to the display controller 21.

Further, the main-body-side first communication circuit BC1 receives various signals transmitted from the probe-side first communication circuit PC1 of the ultrasound probe 1, transmits the signals to the main body controller 23, and also transmits various signals transmitted from the main body controller 23 to the probe-side first communication circuit PC1 of the ultrasound probe 1.

The main-body-side second communication circuit BC2 also includes an antenna for transmitting and receiving radio waves, receives various signals transmitted from the probe-side second communication circuit PC2 of the ultrasound probe 1, transmits the signals to the main body controller 23, and also transmits various signals transmitted from the main body controller 23 to the probe-side second communication circuit PC2 of the ultrasound probe 1.

The main-body-side first communication circuit BC1 and the main-body-side second communication circuit BC2 may be configured by sharing or reconfiguring a part or the whole of the circuits corresponding to each other.

The display controller 21 displays, as a display image, the ultrasound image received via the main-body-side first communication circuit BC1, on the monitor 22.

The monitor 22 displays, as a display image, the ultrasound image under a control of the display controller 21, and includes a display device such as a liquid crystal display (LCD) or an organic electroluminescence (EL) display.

The main body controller 23 controls each unit of the apparatus main body 2 based on a program stored in advance in a storage unit (not illustrated) or the like and an input operation which is input by an operator via the input device 26.

The battery 25 supplies power to the display controller 21, the monitor 22, the main body controller 23, the main-body-side first communication circuit BC1, and the main-body-side second communication circuit BC2 in the apparatus main body 2.

The input device 26 is a device that allows an operator to perform an input operation, and can be configured to include a keyboard, a mouse, a trackball, a touch pad, a touch panel, or the like. In a case where a touch sensor is combined with the monitor 22, the touch sensor can be used as the input device 26.

The main-body-side processor 24 including the display controller 21 and the main body controller 23 of the apparatus main body 2 is configured with a CPU and a control program for causing the CPU to perform various processing. On the other hand, the main-body-side processor 24 may be configured using FPGA, DSP, ASIC, GPU, or other ICs, or may be configured by combining thereof.

In addition, the display controller 21 and the main body controller 23 of the main-body-side processor 24 may be partially or wholly integrated into one CPU or the like.

Here, a power supply mode of the ultrasound probe 1 will be described. The ultrasound probe 1 has two power supply modes including an active mode in which an operation of the ultrasound unit 15 is enabled and a standby mode in which an operation of the ultrasound unit 15 is disabled and the power consumption is lower than the power consumption in the active mode. In addition, the standby mode has two types of modes, a first mode and a second mode in which the power consumption is lower than the power consumption in the first mode.

In the active mode and the first mode, it is assumed that the ultrasound probe 1 and the apparatus main body 2 are in a paired state, and in the second mode, it is assumed that the ultrasound probe 1 and the apparatus main body 2 are in an unpaired state in which pairing is not yet performed. Here, pairing refers to processing of allowing the ultrasound probe 1 and the apparatus main body 2 to perform wireless communication with each other by performing registration, authentication, and the like.

In the active mode, as illustrated in FIG. 1, the power supply controller 16 closes the first switch SW1 and opens the second switch SW2.

By closing the first switch SW1, power is supplied from the battery 18 to the ultrasound unit 15 and the probe-side first communication circuit PC1, and thus the ultrasound unit 15 and the probe-side first communication circuit PC1 enter into an operable state. Therefore, by operating the ultrasound unit 15, transmission and reception of ultrasound waves are performed, and thus the ultrasound image data can be acquired. Further, the acquired ultrasound image data can be transmitted from the probe-side first communication circuit PC1 to the main-body-side first communication circuit BC1 of the apparatus main body 2 using, for example, a Wi-Fi communication method.

In addition, by opening the second switch SW2, power supply from the battery 18 to the probe-side second communication circuit PC2 is stopped, and thus the probe-side second communication circuit PC2 enters into an operation-prohibited state.

Therefore, in the active mode, transmission and reception of various signals are performed between the probe controller 14 of the ultrasound probe 1 and the main body controller 23 of the apparatus main body 2 via the probe-side first communication circuit PC1 and the main-body-side first communication circuit BC1.

Figure 4:
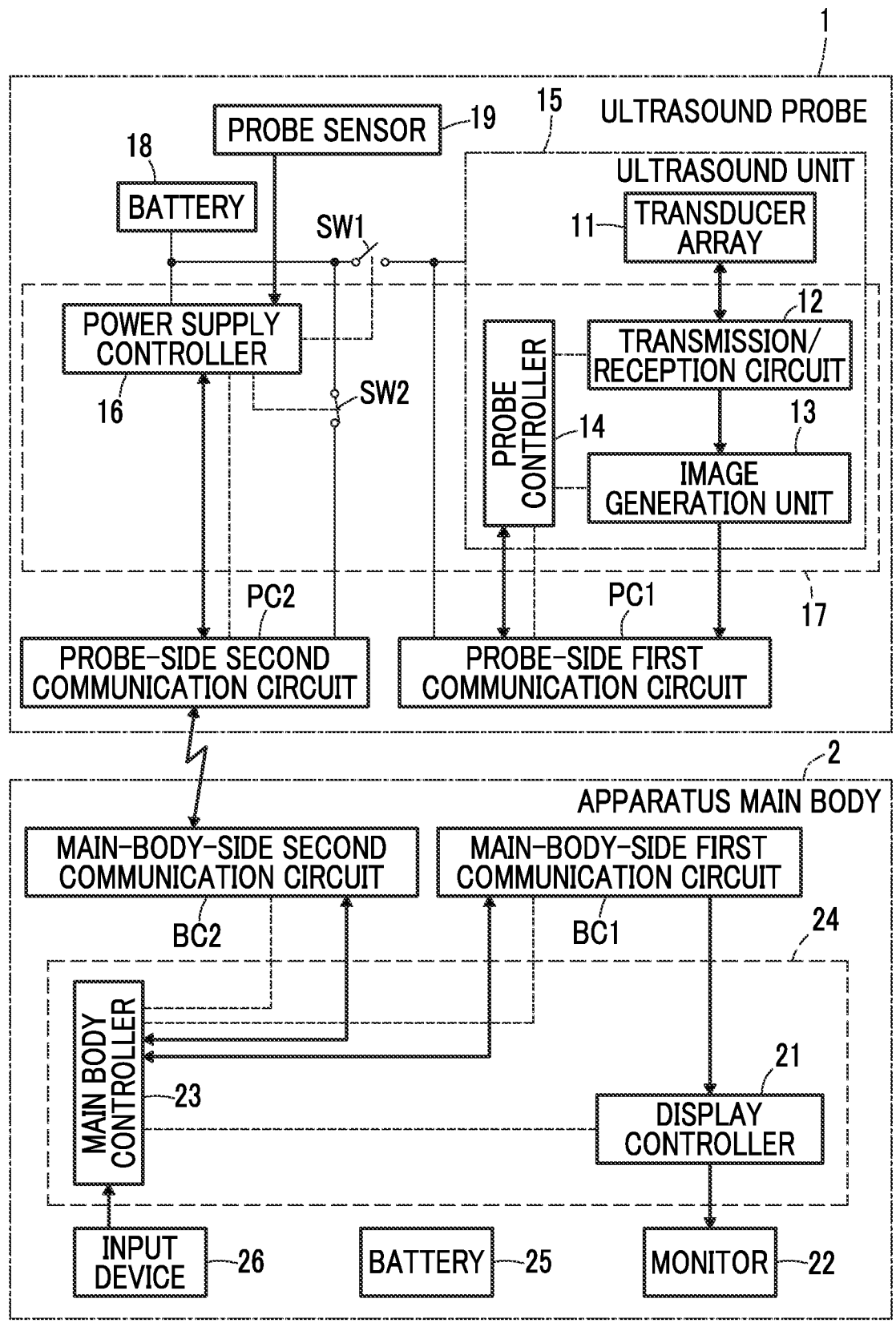
FIG. 4 is a block diagram illustrating a configuration of the ultrasound diagnostic apparatus according to the embodiment 1 in a first mode.

On the other hand, in the first mode among the first mode and the second mode included in the standby mode, as illustrated in FIG. 4, the power supply controller 16 opens the first switch SW1 and closes the second switch SW2.

By opening the first switch SW1, power supply from the battery 18 to the ultrasound unit 15 and the probe-side first communication circuit PC1 is stopped, and thus the ultrasound unit 15 and the probe-side first communication circuit PC1 enter into an operation-prohibited state. Therefore, the ultrasound unit 15 cannot acquire the ultrasound image data.

In addition, by closing the second switch SW2, power is supplied from the battery 18 to the probe-side second communication circuit PC2, and thus the probe-side second communication circuit PC2 enters into an operable state.

Therefore, in the first mode, transmission and reception of various signals are performed between the power supply controller 16 of the ultrasound probe 1 and the main body controller 23 of the apparatus main body 2 via the probe-side second communication circuit PC2 and the main-body-side second communication circuit BC2.

In this way, in the first mode, not only the ultrasound unit 15 enters into an operation-prohibited state, but also the probe-side first communication circuit PC1 using, for example, Wi-Fi with a high power consumption enters into an operation-prohibited state. Thus, the power consumption of the ultrasound probe 1 in the first mode is lower than the power consumption in the active mode.

In the first mode, power is not supplied from the battery 18 to the ultrasound unit 15 and the probe-side first communication circuit PC1, while power is supplied from the battery 18 to the power supply controller 16 and the probe-side second communication circuit PC2. Thus, in a case where the power supply controller 16 receives an activation instruction signal from the apparatus main body 2 via the probe-side second communication circuit PC2, a transition from the first mode to the active mode can be started.

In addition, in the second mode among the first mode and the second mode included in the standby mode, as illustrated in FIG. 5, the power supply controller 16 opens both the first switch SW1 and the second switch SW2. Since the first switch SW1 and the second switch SW2 are open, not only power supply from the battery 18 to the ultrasound unit 15 and the probe-side first communication circuit PC1 is stopped, but also power supply from the battery 18 to the probe-side second communication circuit PC2 is stopped. Thereby, the ultrasound unit 15, the probe-side first communication circuit PC1, and the probe-side second communication circuit PC2 enter into an operation-prohibited state, and thus the ultrasound probe 1 enters into a so-called sleep state.

Therefore, the power consumption of the ultrasound probe 1 in the second mode is further lower than the power consumption in the first mode.

In the second mode, both the probe-side first communication circuit PC1 and the probe-side second communication circuit PC2 enter into an operation-prohibited state, and the ultrasound probe 1 and the apparatus main body 2 are in an unpaired state. Thus, the ultrasound probe 1 cannot receive a signal from the apparatus main body 2. On the other hand, power is supplied from the battery 18 to the power supply controller 16. Thus, in a case where a detection signal obtained by detecting that the ultrasound probe 1 is gripped or moved is input from the probe sensor 19, the power supply controller 16 can start a transition from the second mode to the active mode.

Next, an operation of the ultrasound diagnostic apparatus according to the embodiment 1 in the active mode will be described with reference to a flowchart of FIG. 6.

First, in step S1, an examination portion of a subject is imaged by the ultrasound unit 15, and thus the ultrasound image data is acquired.

At this time, under a control of the probe controller 14, transmission and reception of ultrasound waves from the plurality of transducers of the transducer array 11 are started according to the drive signal from the pulser 31 of the transmission/reception circuit 12. The ultrasound echo reflected by an internal body tissue of the subject is received by the plurality of transducers of the transducer array 11, and thus a reception signal is output to the amplification unit 32. The reception signal is amplified by the amplification unit 32, and the amplified signal is converted into a digital signal by AD conversion of the AD conversion unit 33. Then, reception focus processing is performed on the digital signal by the beam former 34, and thus a sound wave signal is generated.

In addition, the sound wave signal is transmitted to the image generation unit 13, attenuation correction according to a depth of a reflection position of the ultrasound wave and envelope detection processing are performed on the sound wave signal by the signal processing unit 41. The sound wave signal is converted into an image signal conforming to a scanning method of a normal television signal by the DSC 42, and various required image processing such as gradation processing is performed on the image signal by the image processing unit 43. In this way, ultrasound image data representing an ultrasound image is generated by the image generation unit 13.

In subsequent step S2, the ultrasound image data is wirelessly transmitted from the ultrasound probe 1 to the apparatus main body 2. At this time, since the probe-side first communication circuit PC1 is in an operable state, the ultrasound image data acquired by the ultrasound unit 15 is transmitted from the probe-side first communication circuit PC1 to the main-body-side first communication circuit BC1 of the apparatus main body 2 by using, for example, Wi-Fi.

Then, in step S3, the ultrasound image data received by the main-body-side first communication circuit BC1 of the apparatus main body 2 is displayed on the monitor 22 via the display controller 21.

Thereafter, in step S4, it is determined whether or not the ultrasound examination is completed. In a case where it is determined that the examination is not yet completed, the process returns to step S1, and processing of step S1 to step S3 is repeated. In a case where it is determined that the examination is completed, a series of processing is ended.

Next, an activation operation of the ultrasound diagnostic apparatus according to the embodiment 1 from the first mode will be described with reference to a flowchart of FIG. 7.

In the first mode, power supply from the battery 18 to the ultrasound unit 15 and the probe-side first communication circuit PC1 is stopped, and the ultrasound unit 15 and the probe-side first communication circuit PC1 enter into an operation-prohibited state. On the other hand, power is supplied from the battery 18 to the power supply controller 16 and the probe-side second communication circuit PC2, and the probe-side second communication circuit PC2 enters into an operable state.

Therefore, in step S5, the power supply controller 16 confirms whether or not an activation instruction signal is received from the apparatus main body 2 via the probe-side second communication circuit PC2. In a case where an activation instruction signal as an activation control signal is transmitted from the main-body-side second communication circuit BC2 by the main body controller 23 of the apparatus main body 2 using BLE and the activation instruction signal received by the probe-side second communication circuit PC2 is input to the power supply controller 16, in step S6, the power supply controller 16 stops power supply from the battery 18 to the probe-side second communication circuit PC2 by opening the second switch SW2 that has been closed so far.

Further, in step S7, the power supply controller 16 supplies power from the battery 18 to the ultrasound unit 15 and the probe-side first communication circuit PC1 by closing the first switch SW1 that has been opened so far. In step S8, wireless communication using, for example, a Wi-Fi communication method is started between the probe-side first communication circuit PC1 and the main-body-side first communication circuit BC1.

In this way, the ultrasound probe 1 is activated from the first mode, and transitions to the active mode illustrated in FIG. 1.

Next, an activation operation of the ultrasound diagnostic apparatus according to the embodiment 1 from the second mode will be described with reference to a flowchart of FIG. 8.

In the second mode, power supply from the battery 18 to the ultrasound unit 15, the probe-side first communication circuit PC1, and the probe-side second communication circuit PC2 is stopped, and the ultrasound unit 15, the probe-side first communication circuit PC1, and the probe-side second communication circuit PC2 enter into an operation-prohibited state.

On the other hand, power is supplied from the battery 18 to the power supply controller 16. In step S9, the power supply controller 16 confirms whether or not a detection signal indicating a detection result that the ultrasound probe 1 is gripped or moved is input from the probe sensor 19.

In a case where the ultrasound probe 1 is gripped or moved by the user, a detection signal from the probe sensor 19 is input to the power supply controller 16. In step S10, the power supply controller 16 closes the second switch SW2 that is opened so far, and thus power is supplied from the battery 18 to the probe-side second communication circuit PC2. Thereby, the ultrasound probe 1 has the same circuit configuration as the circuit configuration in the first mode illustrated in FIG. 4.

In subsequent step S11, the power supply controller 16 transmits a pairing request signal from the probe-side second communication circuit PC2 to the main-body-side second communication circuit BC2 of the apparatus main body 2 by using BLE. In step S12, the power supply controller 16 confirms whether or not a pairing completion notification signal is received from the apparatus main body 2 via the probe-side second communication circuit PC2.

Processing of step S9 to step S12 is repeated until a pairing completion notification signal is received from the apparatus main body 2.

In addition, in a case where a pairing completion notification signal as an activation control signal is transmitted from the main-body-side second communication circuit BC2 by the main body controller 23 of the apparatus main body 2 using BLE, and where a pairing completion notification signal received by the probe-side second communication circuit PC2 is input to the power supply controller 16, the power supply controller 16 executes transition processing to the active mode through processing of step S6 to step S8 as in the activation operation from the first mode.

That is, in step S6, the power supply controller 16 stops power supply from the battery 18 to the probe-side second communication circuit PC2 by opening the second switch SW2. In step S7, the power supply controller 16 supplies power from the battery 18 to the ultrasound unit 15 and the probe-side first communication circuit PC1 by closing the first switch SW1. In step S8, wireless communication using, for example, a Wi-Fi communication method is started between the probe-side first communication circuit PC1 and the main-body-side first communication circuit BC1.

Thereby, the ultrasound probe 1 is activated from the second mode, and transitions to the active mode illustrated in FIG. 1.

As described above, depending on whether the ultrasound probe 1 is in the active mode, the first mode, or the second mode, the power supply controller 16 selects one of the probe-side first communication circuit PC1 with a large transmission capacity and a high power consumption and the probe-side second communication circuit PC2 with a small transmission capacity and a low power consumption, and the ultrasound probe 1 performs wireless communication with the apparatus main body 2 by using the selected communication circuit. Thus, it is possible to activate the ultrasound probe 1 only by an operation of the apparatus main body 2 and achieve power saving.

Figure 8:
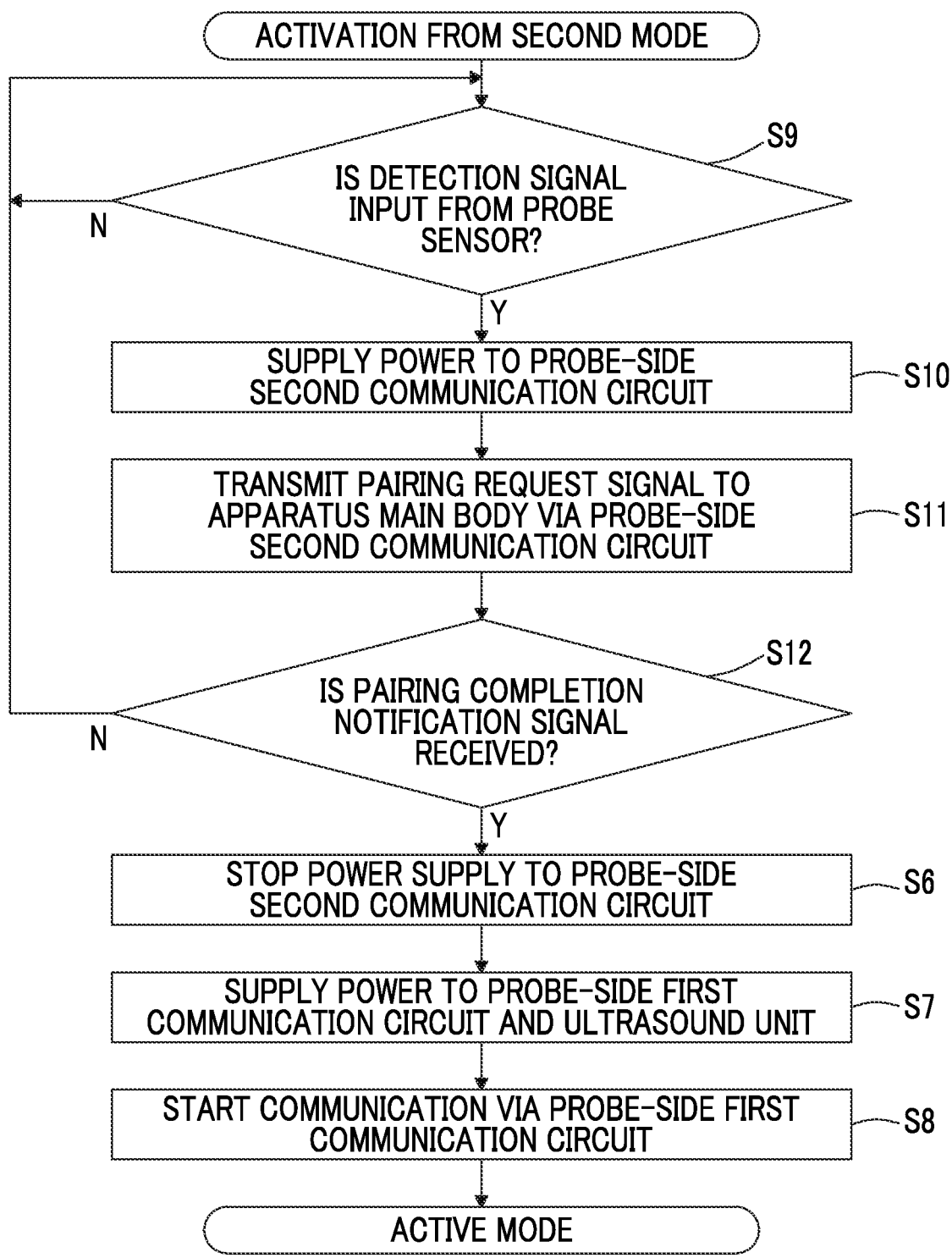
FIG. 8 is a flowchart illustrating an operation of the ultrasound diagnostic apparatus according to the embodiment 1 in a case of being activated from the second mode.

As can be seen from the flowcharts of FIG. 7 and FIG. 8, a time required to transition the power supply mode from the first mode to the active mode is shorter than a time required to transition the power supply mode from the second mode to the active mode.

Further, in the embodiment 1 described above, the image generation unit 13 is provided in the ultrasound probe 1. On the other hand, the present invention is not limited thereto, and the image generation unit 13 can also be provided in the apparatus main body 2. In this case, the ultrasound unit 15 of the ultrasound probe 1 is configured with the transducer array 11, the transmission/reception circuit 12, and the probe controller 14, and the sound wave signal acquired by the transmission/reception circuit 12 is transmitted as the ultrasound image data from the ultrasound probe 1 to the apparatus main body 2. In the apparatus main body 2, the ultrasound image data generated by the image generation unit 13 is displayed on the monitor 22 via the display controller 21.

Embodiment 2

In the embodiment 1 described above, in the second mode, the ultrasound unit 15, the probe-side first communication circuit PC1, and the probe-side second communication circuit PC2 enter into an operation-prohibited state. On the other hand, the present invention is not limited thereto.

For example, as in the first mode, the ultrasound unit 15 and the probe-side first communication circuit PC1 enter into an operation-prohibited state, while power is supplied from the battery 18 to the probe-side second communication circuit PC2. Thus, it is possible to set the second mode in which the probe-side second communication circuit PC2 enters into an operable state and the power supply controller 16 controls the probe-side second communication circuit PC2 such that the ultrasound probe 1 performs wireless communication with the apparatus main body 2 at a communication interval longer than a communication interval in the first mode.

The probe-side second communication circuit PC2 is controlled to perform wireless communication at the communication interval longer than the communication interval in the first mode. Thus, it is possible to realize the second mode with a lower power consumption than the power consumption of the ultrasound probe 1 in the first mode.

Even in this case, as in the activation operation from the second mode according to the embodiment 1, in a case where the detection signal from the probe sensor 19 is input to the power supply controller 16, transition processing to the active mode can be started. In addition, the probe-side second communication circuit PC2 enters into an operable state even though the communication interval is longer than the communication interval in the first mode. Thus, as in the activation operation from the first mode according to the embodiment 1, in a case where the activation instruction signal transmitted from the main-body-side second communication circuit BC2 of the apparatus main body 2 is input to the power supply controller 16 via the probe-side second communication circuit PC2, transition processing to the active mode can be started.

In the embodiment 2, in the second mode, the power supply controller 16 controls the probe-side second communication circuit PC2 such that the ultrasound probe 1 performs wireless communication with the apparatus main body 2 at the communication interval longer than the communication interval in the first mode. On the other hand, the ultrasound probe 1 may include a probe-side third communication circuit that is configured to perform wireless communication at a long communication interval which is set in advance. The power supply controller 16 selects one of three communication circuits including the probe-side first communication circuit PC1, the probe-side second communication circuit PC2, and the probe-side third communication circuit according to the power supply mode of the ultrasound probe 1. Thus, the ultrasound probe 1 can perform wireless communication with the apparatus main body 2 by using the selected communication circuit.

In the embodiment 1 and the embodiment 2, as the apparatus main body 2, a portable or handheld compact apparatus main body can be used, and a stationary apparatus main body can also be used. The apparatus main body 2 may also be configured to use power from a commercial power source without including the built-in battery 25.

EXPLANATION OF REFERENCES

1: ultrasound probe
2: apparatus main body
11: transducer array
12: transmission/reception circuit
13: image generation unit
14: probe controller
15: ultrasound unit
16: power supply controller
17: probe-side processor
18: battery
19: probe sensor
21: display controller
22: monitor
23: main body controller
24: main-body-side processor
25: battery
26: input device
31: pulser
32: amplification unit
33: AD conversion unit
34: beam former
41: signal processing unit
42: DSC
43: image processing unit
SW1: first switch
SW2: second switch
PC1: probe-side first communication circuit
PC2: probe-side second communication circuit
BC1: main-body-side first communication circuit
BC2: main-body-side second communication circuit

What is claimed is:

1. An ultrasound diagnostic apparatus comprising:
an ultrasound probe; and
an apparatus main body that is wirelessly connected to the ultrasound probe,
wherein the ultrasound probe includes
an ultrasound processor that acquires ultrasound image data by transmitting and receiving ultrasound waves,
a plurality of probe-side communication circuits each of which performs wireless communication with the apparatus main body and which have transmission capacities different from each other and power consumptions different from each other, and
a power supply control processor that selects one probe-side communication circuit among the plurality of probe-side communication circuits according to a power supply mode of the ultrasound probe and performs wireless communication with the apparatus main body by using the selected probe-side communication circuit,
the power supply mode of the ultrasound probe includes an active mode in which an operation of the ultrasound processor is enabled and a standby mode in which an operation of the ultrasound processor is disabled and a power consumption is lower than a power consumption in the active mode, and the power supply control processor switches the power supply mode from the standby mode to the active mode in a case where the ultrasound probe receives an activation control signal from the apparatus main body.

2. The ultrasound diagnostic apparatus according to claim 1,
wherein the plurality of probe-side communication circuits include
a probe-side first communication circuit that is selected by the power supply control processor and transmits the ultrasound image data acquired by the ultrasound processor to the apparatus main body in a case where the power supply mode is the active mode, and
a probe-side second communication circuit that is selected by the power supply control processor and operates with a power consumption lower than a power consumption of the probe-side first communication circuit in a case where the power supply mode is the standby mode.

3. The ultrasound diagnostic apparatus according to claim 2,
wherein the ultrasound probe includes a built-in battery, the power supply control processor supplies power from the battery to the ultrasound processor and the probe-side first communication circuit and stops power supply to the probe-side second communication circuit in a case where the power supply mode is the active mode, and
the power supply control processor supplies power from the battery to the probe-side second communication circuit and stops power supply to the ultrasound processor and the probe-side first communication circuit in a case where the power supply mode is the standby mode.

4. The ultrasound diagnostic apparatus according to claim 3,
wherein the standby mode further includes a first mode and a second mode in which a power consumption is lower than a power consumption in the first mode,
the power supply control processor supplies power from the battery to the probe-side second communication circuit in a case where the power supply mode is the first mode, and
the power supply control processor stops power supply from the battery to the probe-side second communication circuit in a case where the power supply mode is the second mode.

5. The ultrasound diagnostic apparatus according to claim 3,
wherein the standby mode further includes a first mode and a second mode in which a power consumption is lower than a power consumption in the first mode,
the power supply control processor supplies power from the battery to the probe-side second communication circuit in a case where the power supply mode is the first mode and in a case where the power supply mode is the second mode, and
the power supply control processor controls the probe-side second communication circuit in a case where the power supply mode is the second mode such that the ultrasound probe performs wireless communication with the apparatus main body at a communication interval longer than a communication interval in a case where the power supply mode is the first mode.

6. The ultrasound diagnostic apparatus according to claim 4,
wherein the ultrasound probe includes a probe sensor for detecting that the ultrasound probe is gripped or moved by a user,
in a case where the power supply mode is the second mode and the probe sensor detects that the ultrasound probe is gripped or moved, the power supply control processor switches the power supply mode from the second mode to the first mode, and the ultrasound probe transmits a pairing request signal to the apparatus main body via the probe-side second communication circuit, and
the power supply control processor switches the power supply mode from the standby mode to the active mode in a case where the ultrasound probe receives a pairing completion notification signal as the activation control signal from the apparatus main body via the probe-side second communication circuit.

7. The ultrasound diagnostic apparatus according to claim 6,
wherein the probe sensor consists of an acceleration sensor or a contact sensor provided on the ultrasound probe.

8. The ultrasound diagnostic apparatus according to claim 5,
wherein the ultrasound probe includes a probe sensor for detecting that the ultrasound probe is gripped or moved by a user,
in a case where the power supply mode is the second mode and the probe sensor detects that the ultrasound probe is gripped or moved, the power supply control processor switches the power supply mode from the second mode to the first mode, and the ultrasound probe transmits a pairing request signal to the apparatus main body via the probe-side second communication circuit, and
the power supply control processor switches the power supply mode from the standby mode to the active mode in a case where the ultrasound probe receives a pairing completion notification signal as the activation control signal from the apparatus main body via the probe-side second communication circuit.

9. The ultrasound diagnostic apparatus according to claim 8,
wherein the probe sensor consists of an acceleration sensor or a contact sensor provided on the ultrasound probe.

10. The ultrasound diagnostic apparatus according to claim 4,
wherein the power supply control processor switches the power supply mode from the standby mode to the active mode in a case where the power supply mode is the first mode and the ultrasound probe receives an activation instruction signal as the activation control signal from the apparatus main body via the probe-side second communication circuit.

11. The ultrasound diagnostic apparatus according to claim 5,
wherein the power supply control processor switches the power supply mode from the standby mode to the active mode in a case where the power supply mode is the first mode and the ultrasound probe receives an activation instruction signal as the activation control signal from the apparatus main body via the probe-side second communication circuit.

12. The ultrasound diagnostic apparatus according to claim 4, wherein a time required to transition the power supply mode from the first mode to the active mode is shorter than a time required to transition the power supply mode from the second mode to the active mode.

13. The ultrasound diagnostic apparatus according to claim 5,
wherein a time required to transition the power supply mode from the first mode to the active mode is shorter than a time required to transition the power supply mode from the second mode to the active mode.

14. The ultrasound diagnostic apparatus according to claim 6,
wherein a time required to transition the power supply mode from the first mode to the active mode is shorter than a time required to transition the power supply mode from the second mode to the active mode.

15. The ultrasound diagnostic apparatus according to claim 8,
wherein a time required to transition the power supply mode from the first mode to the active mode is shorter than a time required to transition the power supply mode from the second mode to the active mode.

16. The ultrasound diagnostic apparatus according to claim 2,
wherein the apparatus main body includes a plurality of main-body-side communication circuits corresponding to the plurality of probe-side communication circuits, and
the plurality of main-body-side communication circuits include
a main-body-side first communication circuit that performs wireless communication with the probe-side first communication circuit, and
a main-body-side second communication circuit that performs wireless communication with the probe-side second communication circuit.

17. The ultrasound diagnostic apparatus according to claim 16,
wherein the activation control signal is transmitted from the apparatus main body to the ultrasound probe via the main-body-side second communication circuit and the probe-side second communication circuit.

18. The ultrasound diagnostic apparatus according to claim 3,
wherein the apparatus main body includes a plurality of main-body-side communication circuits corresponding to the plurality of probe-side communication circuits, and
the plurality of main-body-side communication circuits include
a main-body-side first communication circuit that performs wireless communication with the probe-side first communication circuit, and
a main-body-side second communication circuit that performs wireless communication with the probe-side second communication circuit.

19. The ultrasound diagnostic apparatus according to claim 18,
wherein the activation control signal is transmitted from the apparatus main body to the ultrasound probe via the main-body-side second communication circuit and the probe-side second communication circuit.

20. A control method for an ultrasound diagnostic apparatus including an ultrasound probe, which includes a plurality of probe-side communication circuits having transmission capacities different from each other and power consumptions different from each other, and an apparatus main body which is wirelessly connected to the ultrasound probe, the method comprising:
selecting one probe-side communication circuit among the plurality of probe-side communication circuits according to a power supply mode of the ultrasound probe; and
performing wireless communication between the ultrasound probe and the apparatus main body by using the selected probe-side communication circuit,
wherein the power supply mode of the ultrasound probe includes an active mode in which an operation of an ultrasound processor is enabled and a standby mode in which an operation of the ultrasound processor is disabled and a power consumption is lower than a power consumption in the active mode, the ultrasound processor acquiring ultrasound image data by transmitting and receiving ultrasound waves, and
the power supply mode is switched from the standby mode to the active mode in a case where the ultrasound probe receives an activation control signal from the apparatus main body.

* * * * *